United States Patent
Maes

(10) Patent No.: US 6,846,648 B2
(45) Date of Patent: Jan. 25, 2005

(54) METHOD FOR THE RAPID DETECTION OF WHOLE MICROORGANISMS ON RETAINING MEMBRANES BY USE OF CHAOTROPIC AGENTS

(75) Inventor: Roland Maes, Mutzig (FR)

(73) Assignee: Anda Biologicals, S.A., Stasbourg (FR)

( * ) Notice: Subject to any disclaimer, the term of this patent is extended or adjusted under 35 U.S.C. 154(b) by 336 days.

(21) Appl. No.: 10/182,793

(22) PCT Filed: Jan. 26, 2001

(86) PCT No.: PCT/EP01/00829

§ 371 (c)(1),
(2), (4) Date: Jul. 30, 2002

(87) PCT Pub. No.: WO01/57532

PCT Pub. Date: Aug. 9, 2001

(65) Prior Publication Data

US 2003/0022160 A1 Jan. 30, 2003

(30) Foreign Application Priority Data

Feb. 1, 2000 (EP) ............................................. 00870013

(51) Int. Cl.$^7$ ............................ C12Q 1/04; C12Q 1/18; C12M 1/00
(52) U.S. Cl. .......................... 435/34; 435/32; 435/308.1
(58) Field of Search .................... 435/34, 32, 308.1, 435/810

(56) References Cited

U.S. PATENT DOCUMENTS

| | | | |
|---|---|---|---|
| 4,695,537 A | | 9/1987 | Dorsett |
| 4,808,518 A | | 2/1989 | Dorsett et al. |
| 4,978,613 A | * | 12/1990 | Bieniarz et al. ............. 435/18 |
| 5,155,023 A | | 10/1992 | Frazer et al. |
| 5,420,017 A | * | 5/1995 | Tuompo et al. ............. 435/29 |
| 5,482,834 A | * | 1/1996 | Gillespie ..................... 435/6 |
| 5,714,343 A | | 2/1998 | Tuompo et al. |

FOREIGN PATENT DOCUMENTS

| | | |
|---|---|---|
| EP | 0234941 | 9/1987 |
| EP | 0325045 | 7/1989 |

* cited by examiner

Primary Examiner—Jean C. Witz
Assistant Examiner—Susan Hanley
(74) Attorney, Agent, or Firm—Knobbe, Martens, Olson & Bear, LLP

(57) ABSTRACT

The present invention relates to a method detection of microorganisms concentrated from body fluids as serum, sputum, pericardiac fluid, urine or other fluid on the surface of retaining membranes by specific partners of reaction that bind to antigenic components of the retained organisms is facilitated when the organisms in suspension in body fluids and/or concentrated on the membrane are treated with a high molar concentration of a chaotropic agent as guanidine, urea, isothiocyanate, thiourea.

24 Claims, No Drawings

METHOD FOR THE RAPID DETECTION OF WHOLE MICROORGANISMS ON RETAINING MEMBRANES BY USE OF CHAOTROPIC AGENTS

CROSS-REFERENCE TO RELATED APPLICATIONS

This is the U.S. National Phase under 35 U.S.C. §371 of International Application No. PCT/EP01/00829, filed Jan. 26, 2001, designating the United States and published in English, which claims priority to European Application No. 00870013.0 filed Feb. 1, 2000.

FIELD OF THE INVENTION

The present invention is in the field of diagnostic and is related to a method and kit for the rapid detection of whole microorganisms on retaining membranes by the use of chaotropic agents.

BACKGROUND OF THE INVENTION

Detection of microorganisms in body fluids, water and alimentary products allows diagnostic and prognostic of many infectious diseases. Cells and microorganisms needed for the making of vaccines demands a severe control of the sterility of the produced media, usually achieved by culturing an aliquot of the medium whose sterility one wants to control, in a growth-promoting medium during several days. Said growth and identification of microorganisms are time consuming, difficult and frequently takes two to three weeks before results are available.

For diagnostic purposes, such a method of determination relying on culture of blood sample or of sputum exists, when there is a need to diagnose the presence of mycobacterial entities. The time needed to arrive at a diagnostic conclusion is however very long, extending sometimes to 4 weeks. For other microorganisms, such as the etiological agents of malaria (especially *Plasmodium falciparum*, leishmaniasis, gonorrhea, syphilis, tuberculosis, malaria, tick-borne Lyme disease, as well as meningitis due to a variety of vectors such as *Neisseria, Haemophilus, Streptococcus, Listeria* and *Mycobacterium*, a rapid diagnostic method putting the whole pathogen in evidence does not exist and there is a need for such rapid method.

Rapid methods of detection of antigens and antibodies are now currently in use for antibodies and proteinic and glycoproteinic antigens whose size is sufficiently small for them to be transported in a lateral flow chromatographic system. For larger entities (such as whole bacteria and eukaryotic organisms), this technique is inapplicable because the analytes are too big to move with the flow. These microorganisms of large size are also able to condense on retaining membranes in such a way that the sensitivity of their detection in situ is considerably enhanced.

However, an intolerably high level of false positive or negative results is also observed. The phenomenon of immunological quenching induced by body fluids is well known. This quenching prevents the recognition of the whole organisms by specific binding partners as antibodies and induces false negative results.

STATE OF THE ART

The document EP-0306206 describes a diagnostic device comprising a funnel that channels the fluid under analysis onto a defined part of a filter membrane that retains the analyte. The funnel is thereafter removed and the membrane is further treated by signal-generating materials and other reagents as washing fluids, applied simultaneously to the test area and adjacent area of the membrane. The simultaneous treatment of adjacent area supposedly provides a negative control to assist in detecting non-specific binding and thereby false-positive results. In said document, the sample is confined to a discrete area of the filter and the whole of the filter is then treated with reagent, thereby giving a true negative control. This document mentions water as fluid passing through the restricted aperture and omits to describe the type of membranes used. Such an improved device relying on direct determination of the presence of pathogens on the membrane is indeed applicable only with water. More charged fluids such as serum, accumulated into a single discrete area of the filter tend to clog this filter up, prevent the easy flow-through of subsequently added fluids (such as a wash medium) and cause the succeeding washing fluids, applied to the whole of the membrane, to flow around that area without penetrating it. Further, even with water, the device is specifically developed and meant to visualise false positive cases, thereby indicating that the occurrence of false positive cases is possible, even with water. No such device applied to detect whole microorganisms by direct labelling is in use for body fluids such as serum, cerebrospinal fluid, pericardial fluid, urine or other body fluid.

The use of a chaotropic agent like sodium thiocyanate has been advocated for suspensions of microorganisms in water before their condensing on a membrane filter, but the concentration advocated is 0.04 molar and only water is recognised as a fluid suitable for treatment (document JP-05034350). This teaching addresses the issue of detection of microorganisms in water, whose clumping may be prevented or deliquesced into singly suspended organisms with the help of low concentrations of disrupting agents.

The increase in sensitivity of an immunochemical assay of collagen has been claimed in the presence of a chaotropic agent. Neither urea, nor guanidine are mentioned as suitable, but thiocyanate used at a concentration of 0.1 to 1.6 molar included in the reaction mix is (document WO92/16846). This teaching addresses the issue of collagen solubilised in an assay medium containing a chaotropic agent as isocyanate and recognised by a binding partner.

Similarly, a treatment of a sample with various detergents and a chaotropic agent as urea prior to immunoassay has been claimed to be applicable to blood samples investigated by immunoassay for the presence of viruses as hepatitis C virus (document WO99/06836). In this case, the chaotropic agent is contacted together with different surfactants with the sample under analysis, not as a washing solution, and no attempt is made to detect in a direct way the pathogenic entity condensed on the surface of a membrane, but a lateral flow immunoassay is used in the detection of the analyte present in the treated biological fluid.

The document U.S. Pat. No. 5,714,343 describes a device consisting in absorbing pads surmounted by a retaining membrane. The fluid is passed through the retaining membrane and the microorganisms potentially retained on the membrane are visualised by a chromogenic agent having an oxidation potential such that the reagent can be reduced by microbial dehydrogenase, yielding a visibly coloured product indicative of the presence of microorganisms in the sample. The retaining membrane having pores (0.75 to 1.2 $\mu$m) larger than the dehydrogenase-active microorganisms it is supposed to retain, the capture of the bacteria on such filters is achieved by mechanical retention. The reason for this unlogically great pore-size used at the risk to let a large amount of the analyte pass through the filter, is the possible occurrence of false positive cases with smaller pores, since other reducing compounds than bacteria (e.g. free reducing enzymes, ascorbic acid, glutathione) may then, be retained, yielding false positive results. Further, although the device is said to be useful for water, blood, milk and urine analysis, only physiological water is described in examples 1 to 7.The principal advantage of this method is the signal-generating material, consisting in a chromogen that forms a visible precipitate of formozane after reaction with bacterial dehydrogenase. Growth of the bacteria in vitro for several days after collection on the retaining membrane is therewith avoided, and much time saved. Many bacteria and yeasts as well as leukocytes possess a dehydrogenase activity and the detecting method does not discriminate between them, except for the selective destruction of dehydrogenase synthesised by gram positive bacteria, leaving the dehydrogenase from gram-negative bacteria still active. This selective destruction of dehydrogenase produced by gram-positive bacteria is achieved by either incubation of the sample with octyl glucoside, which suppresses the dehydrogenase activity of all gram+ bacteria tested, or else 0.5 M guanidine, that suppresses the dehydrogenase activity of only some gram+ bacteria while at least one gram-bacterium, *Pseudomonas*, is also affected (only living bacteria possessing active dehydrogenase).

Therefore, one of the drawbacks of said technique is that it does not allow a specific detection, because a large number of microorganisms possessing active dehydrogenase and other reducing enzymes are detected and identified.

The documents U.S. Pat. Nos. 4,695,537 and 4,808,518 underline the fact that hypertonic solutions of agents as sodium chloride, potassium thiocyanate, guanidine and others may be applied to antigens in suspension and to intracellularly located antigens, at concentrations between 1.0 and 5.0 M, preferably between 2.0 and 3.5 M. These concentrations do not reduce the antigenic properties of the antigen but improve the yield.

The document EP 0 234 941 indicates that treatment of viral subunits with denaturing concentrations of guanidine (from 5 to 8 molar) (after the purification of the virus and its disruption into subunits with detergents) improves the purity of these subunits for the adsorption of antibodies in an Elisa. It is known that denaturing concentrations of chaotropic agents destroy protein assemblies into subunits, as is the case with the alpha and beta subunits of human chorionic gonadotropin. Sometimes, as is the case with the subunits of HCG, the immunogenicity of the subunits is not affected by this hypertonic treatment. Tuberculoproteins are isolated by treating tubercular material with chaotropic agents (guanidine, urea and phenol) which reduce the tubercle pathogen to immunogenic tuberculoproteins (FR-2082226). However, these documents do not suggest the maintenance of the pathogen under analysis whole and intact, without any reduction into subunits, so that it remains of a size sufficient to be mechanically retained on a filtering membrane and thereafter its direct detection.

AIMS OF THE INVENTION

The present invention is related to a method and kit for the rapid detection of whole microorganisms, which do not present or reduce the possible false positive or false negative results affecting the method of the state of the art.

SUMMARY OF THE INVENTION

A simple detection system able to demonstrate in a direct way, in a sensitive way and in a specific way the presence of whole pathogens belonging to the bacterial kingdom or else eukaryotic parasites as *Plasmodium falciparum* or toxoplasma in various body fluids as serum, cerebrospinal fluid, pericardial fluid etc. condensed on a retaining membrane, is not yet available, although such a detection would greatly improve the rapid diagnostic of several pathogens. Such a system must, per force, exploit the specific binding capacities existing among specific binding partners for the microorganisms one wishes to detect, as specific antibodies, protein A, protein G.

The occurrence of false positive results are due to contaminating substances present in the body fluids wherein the microorganisms are suspended and quenching induced by them, which adsorbs to the surface of these microorganisms and prevent their recognition by specific binding partners (either when these organisms are in suspension in these body fluids or after, these microorganisms have been condensed out of these fluids, on the surface of retaining membranes).

The present invention is related to a method for the detection of one or more microorganisms present in a liquid sample, preferably a biological liquid sample, said method comprising at least the following steps:

(a) possibly adding to said liquid sample a reagent solution comprising a chaotropic substance having preferably a concentration able to rupture hydrogen bonds;

(b) filtering the liquid sample through a filter having a pore size which is small enough to prevent passage of microorganisms through the filter, but large enough to permit passage of any soluble material present in the sample, whereby the microorganisms are retained on the filter;

(c) possibly passing said reagent solution comprising a chaotropic substance through the filter having the retained microorganisms thereon, said chaotropic agent solution having preferably a concentration able to rupture (suppress) hydrogen bonds, and (d) passing one or several labelled reagents (signal-generating reagents) through the filter, at least one of said reagents being specific for the microorganisms to be detected.

The chactropic agent solution comprises urea, guanidine, thiourea, isothiocyanate or a mixture thereof and the concentration of the chaotropic agent in the solution is higher than 2M, preferably between 4 and 8M (denaturating concentration).

The microorganisms could be present in any biological sample, preferably in a charged biological sample such as sputum, blood, serum, plasma, cephalo-rachidian fluid or urine obtained from any animal patient, including the human and are preferably pathogenic bacteria or eukaryotic parasites detected either simultaneously or successively.

Contaminants of beverages and foods, as listeria, yeasts and molds are also detectable. The type of filter used to retain the analytes under study is usually cellulose, paper, nitrocellulose or nylon, or other types selected by the man skilled in the art.

The specific labelled reagents used for the detection of microorganisms are preferably antibodies, possibly coupled directly or indirectly to a marker, such as gold micellae, biotine, enzymes, chromophores, stained latex beads, enzymes, fluorophores, radioactive compounds or a mixture thereof.

The present invention is related also to a kit comprising means and media for performing the detection method according to the invention, said kit comprising filtering membranes of predetermined pore size to retain specific microorganisms, one or several chaotropic agents, one or several labelled reagents (signal-generating reagents), one of them being specific for the monitored microorganisms.

If necessary, the method and kit could be adapted to allow the rapid detection of microorganisms present in a sample by using an automate and means for performing automatically the specific detection according to the invention.

DETAILED DESCRIPTION OF THE INVENTION

The presence of microorganisms as the Koch's bacillus (*Mycobacterium tuberculosis*), *Plasmodium falciparum*, or other bacteria and parasites difficult to diagnose, as leishmaniasis, gonorrhea, syphilis, tick-borne Lyme disease, as well as meningitis due to a variety of vectors such as *Neisseria, Haemophilus, Streptococcus*, and *Listeria*, and yeasts and worms, is detected in human and animal serum and other body fluids by condensing the microorganisms present in these fluids on the surface of a membrane that allows the passage of the fluid, but retains the microorganisms on its surface. Thereafter by washing the membrane to eliminate contaminants, treating the membrane with a chaotropic agent as guanidine, urea, guanidine isothiocyanate or similar agent, at a concentration high enough to clean the microorganisms of all the quenching elements that prevent their recognition by specific binding partners, treat the retaining membrane and the microorganisms condensed on its surface with a binding partner specific for the microorganism, such as antibodies, thereafter one washes the membrane free of excess binding reagent and label the antibodies bound to the microorganism with a binding partner specific for the class of gammaglobulins of the animal species in which antibodies against the microorganism were raised, e.g. rabbit, goat, donkey, as antibodies against rabbit or goat or donkey gammaglobulins, protein A or protein Gj, said binding partner being itself coupled to a marker (i.e. an agent susceptible to amplify the labelling, as colloidal gold or end enzyme).

The detection of microorganisms having the size of bacteria or bigger, (spirochetes, trypanosomes and worms) present-in body fluids as serum and urine obtained by means of specific binding partners as antibodies, protein A or protein G is not easy.

However microorganisms in solution or condensed on the surface of a membrane resist the disruptive action of high molar concentrations of chaotropic agents as guanidine, urea, thiocyanate, thiourea, isothiocyanate, perchlorate etc. while becoming readily accessible therewith to recognition by specific binding partners. The same microorganisms condensed from the same sera on the same retaining membranes and treated with the same chaotropic agents used at a molarity too low to exploit their disruptive potential on proteins (as for example 0.5 molar guanidine used to destroy the activity of gram+bacterial dehydrogenase) are not recognised by their specific binding partners. Therefore a tenfold higher concentration of the chaotropic agents is unexpectedly beneficial in the conduct of an immunoassay.

Molarities of urea and guanidine ranging from about 4 to 8 are needed to have an effect. With other chaotropic agents, as thiourea and isocyanate, lower concentrations ranging between 2 and 5 molar, are adequate.

High molar concentrations of chaotropic agents as guanidine and urea have been for a long time applied, mostly together with organic solvents as phenol and chloroform, to liberate the nucleic acids DNA and RNA from eukaryotic cells, from bacterial cells as *Escherichia coli* and from virus entities. The fact that nucleic acid is obtained following treatment of cells and viruses with chaotropic agents indicates that the cell membranes, the nuclear membranes and tertiary structures of proteins in viruses are destroyed by this treatment. This effect precludes any evident application of chaotropic agents at high molar concentrations for the purpose of the present invention.

Chaotropic agents as urea and guanidine applied at concentrations ranging between 4 to 8 molar, useful and necessary for the exploitation of their protein denaturing properties and their ability to suppress hydrogen bonds, are currently used either to eliminate proteins from nucleic acid preparations or else to separate protein subunits, thereafter isolated by separation methods based on the different physico-chemical properties of the separated products. For example, the alpha and beta subunits of chorionic gonadotropin are separated in the presence of 8 molar urea at 40° C. and the two subunits are subsequently isolated by passage on a DEAE-cellulose chromatography column. Purified tuberculoproteins are isolated by submitting tubercular material to a precipitation stage at an acid pH, carried out in the presence of a substance capable of rupturing hydrogen bonds, as urea, guanidine, formamide, phenol, etc. The precipitated material is thereafter contacted with a modified cellulose bearing a basic group such as DEAE (see document FR-2082226). In these cases, the molarity of the chaotropic substance is sufficiently high to exploit its disrupting properties on substances kept in solution, with the purpose to effectuate a separation and solubilisation of the various substances contained within the original preparation.

The main problem encountered in the development of assays aiming at detecting in a direct way pathogens condensed on a retaining membrane is the quenching induced by charged liquid media as serum, quenching of such a nature that the microorganism is not anymore readily recognised by specific binding partners. Many sera induce a quenching that considerably reduces the signal that is detected after application of signal-producing elements. More particularly, the pathogen isolated from some sera and condensed at the surface of the retaining membrane does not react to antibodies directed against it, which precludes the possibility to thereafter visualise the presence of these antibodies by signal-amplifying binding partners as gold-labelled protein A or as peroxidase-labelled antibodies specifically binding with gammaglobulins. Whereas some sera and less charged fluids as urine, culture media and water are satisfactory in this sense, the fact that some sera induce false-negative results precludes the routine use of such methods for the determination of the presence of pathogens.

Quite unexpectedly, it was discovered that high molar concentrations of chaotropic agents as guanidine, urea, thiourea, isocyanate, applied directly on the liquid sample under analysis and/or on the retaining membrane following the condensing of the microorganism on its surface, greatly facilitates the reaction of specific binding partners with the microorganism under analysis. A device consisting in a cartridge containing absorbent pads, topped with a retaining membrane, is currently available for the making of such assays as described in the document U.S. Pat. No. 5,714,343 incorporated herein by reference. Using such a device, the following experiments were done, which may serve as examples.

EXAMPLE 1

500 µl of human serum spiked with tuberculous bacillus was passed over a membrane whose mean pore size was 0.45 microns. This pore size is small enough to retain the great majority of the *bacilli*, whose mean size is 0.6×4 µm. After passage of the liquid sample, the retaining membrane was washed with 200 μl of washing medium. The membrane was further washed with 200 μl of a 6 molar solution of guanidine hydrochloride at pH 8.0. A 200 μl wash with washing medium eliminated the quanidine and the membrane was thereafter treated with 100 μl of a dilute solution of rabbit antibodies against mycobacterium tuberculosis. The antibodies were obtained in rabbits repeatedly inoculated with heat-killed Mycobacterium tuberculosis (Difco). After a 200 μl wash, 100.μl of gold-labelled protein A at a concentration of $A_{520}$=0.75 were applied, with a positive result consisting in a red-pink spot in the middle of the membrane.

The same analysis performed in the absence of a chaotropic reagent produced a diffuse barely coloured spot instead.

The same analysis performed with a solution of guanidine whose concentration was lowered to about 4.5 moles yielded a spot whose intensity was similar to the positive control (6 molar guanidine).

The same analysis performed with a solution of guanidine whose concentration was increased to 7 moles yielded a spot whose intensity was similar to that obtained with about 6 molar concentration in guanidine.

EXAMPLE 2

An analysis identical to that described in Example 1 was performed with a solution that was 7 molar in urea. The same positive result as in example 1 was obtained, whereas concentrations lower than about 4.5 molar were ineffective in revealing a satisfactory signal. A concentration of urea superior to about 8 molar reduced the signal.

EXAMPLE 3

The same experiment as in Example 1 was conducted, with the guanidine wash solution brought to pH 4.0, 5.0, 6.0, 7.0, 8.0, 9.0, 10.0, 11.0, 12.0 and 13.0 with concentrated HCl or 10 molar NaOH. The solutions of the chaotropic agent that were of an acidity equal or inferior to pH 6.0 were much less satisfactory that those whose pH was above neutrality. At a basic pH 13.0, the signal was reduced. Optimal signal delivery was obtained with a solution of guanidine at pH 9.0.

EXAMPLE 4

The same experiment as in example 1 was conducted with the chaotropic agents 4 molar potassium thiocyanate, 2 molar thiourea, 6 molar guanidine containing 2 molar thiourea, 3 molar urea mixed with 3 molar guanidine. Solubilisation difficulties due to the presence of various surfactants currently used in immunoassays and known from the man of the art did not allow higher molarities, concentrations for thiocyanate and thiourea than those here applied. These chaotropic agents were not superior to urea or quanidine used alone.

EXAMPLE 5

These experiments showed that, when no sputum is used, a membrane with a pore size 0.45 μm has a satisfactory retention power. However, when sputum is used, the 0.45 μm pore sized membrane tends to clog up easier. A membrane with a larger pore size is preferable. To further favour flow, a glass fiber pre-filter is needed, that retains undissolved matter and viscous matter present in sputum.

Sputum from a TB *tuberculosis* patient was collected at the Pneumology department of the University Hospital of Strasbourg (France). The sputum underwent regular analysis and was found to contain TB bacilli by the bacilloscopy technique based on the Ziehl-Nielsen Stain. The sputum was fluidised by addition of 0.25% N-acetyl-cysteine and 1% NaOH (final concentrations). This fluidising method is standard in mycobacteriology for the treatment of sputum before its use in cultures. The NaOH is added as a fluidisation medium and also in order to decontaminate the sample and kill all other bacteria present, before culture for tubercle bacilli is initiated. The NaOH is not indispensable for the liquefaction and N-acetyl-cysteine, at concentrations between 0.5% and 2% and alkaline pH, is able to liquefy sputum in two minutes. Other methods of fluidisation, based on hypochlorite or sodium dodecyl sulphate, were found to work just as well. In particular, bleach may be appropriate for low income countries because it is cheap, available locally and it better respects the integrity of the retaining membrane than NaOH. An alteration of the retaining membrane, made of nitro-cellulose, was observed when the sample fluid was treated with NaOH at 1%. A neutralisation of the fluid with HCl was needed before passing it on a nitro-cellulose retaining membrane. Other means of fluidisation (bleach, dithiothreitol) proved compatible with the retaining membranes used. Any fluidising agent that respects the antigenicity of the bacteria and does not alter the retaining membrane is satisfactory.

A fiber-glass prefilter pad was placed on top of the nitrocellulose retaining membrane, so as to retain the unsolubilised material remaining in the fluidised sputum. 200 μl of fluidised sputum were passed through the prefilter and the 0.8 μnitrocellulose membrane, before the fiberglass prefilter was removed. The retaining membrane was washed with 2 times 100 μl of 0.2M phosphate pH 7.2 containing 0.2% Tween 20.After the wash, the membrane was treated with 6 M guanidine, and further contacted with a rabbit antiserum against *M. tuberculosis* appropriately diluted 1:160 in phosphate-buffered saline pH 7.2, containing 0.2% Tween 20.After a washing step, the signal present on the membrane amplified with a reagent consisting in 30 nm gold-sensitised rabbit anti-goat IgG. The sensitivity of the system detects about 3000 mycobacterial entities/ml.

EXAMPLE 6

The detection of mycobacteria in sputum was done as in example 5, with a membrane whose pore size was 0.45 μm. This small pore size was found acceptable although it retarded the flow rate, but a slower flow of the reagents enhanced the sensitivity of the method by allowing a longer contact and prolonged reaction time of the reagents with the antigens. Rabbit anti-mycobacterial serum was used to label the antigen retained on the membrane. The secondary partner of reaction was composed of antibodies against rabbit IgG raised in donkeys. The enhancer was 30 nm-gold-labelled Protein G., which reacts well with equine antibodies. The sensitivity reached was about 3000 entities/ml.

EXAMPLE 7

A membrane with a pore-size of 0.45 μm was used to collect the mycobacteria suspended in sputum in an experiment applied as in example 5.After labelling the mycobacteria present on the membrane with specific rabbit antibodies, a secondary binding partner consisting of Protein A-20 nm colloidal gold, was applied (Sigma Chemical Co, St Louis, Mo.). The results were similar to those obtained in example 6, when the secondary antibody was gold-sensitised goat anti-rabbit IgG, i.e. 3000 particles/ml.

EXAMPLE 8

Human infections caused by *Chlamydia trachomatis* primarily involve the eyes and the genital tract. The morphology of the chlamydiae resolves into Elementary Bodies (0.2 to 0.4 µm) that can be detected by immunofluorescence or enzyme linked immunosorbent assays and Reticulate Bodies which is the intracellular, metabolically active form (0.6 to 1.0 µm), rarely observed microscopically The laboratory diagnosis is based on a variety of methods (complement fixation, microimmunofluorescence, enzyme linked immunosorbent assays, direct microscopic examination, isolation of the microorganisms and nucleic acid techniques). For genital tract infections, specimens for assay are urethral and cervical swabs, and urine, with the aim to detect the etiological agent.

Human urine was spiked with decreasing amounts of the pathogen *Chlamydia trachomatis* Elementary bodies. Antibodies raised in rabbits were used to label the pathogen. One and a half millilitres of the spiked urine were passed on a filter with mean more size 0.2 µm, that was able to retain the pathogen on its surface. No prefilter was useful. Revelation of the presence of the pathogen was done by treating the membrane first with 5 M guanidine at pH 8.0, thereafter with the specific antibodies, followed with Gold-protein A, that reacts with rabbit gammaglobulins. In a second analysis, antibodies raised in goats were used. Gold-labelled protein G was used to reveal the presence of the goat antibodies and an enhancer consisting in Gold-labelled pig gammaglobulins was finally applied. The sensitivity of this detection system was compared to that obtained by the rapid test chlamydia, a commercial diagnostic kit (Abbott). Whereas a single amplification system (rabbit antibodies and Gold-protein A) yielded similar results, the use of an enhancer (Gold-labelled pig antibodies) increased the sensitivity two-fold.

EXAMPLE 9

Toxoplasmosis is caused by *Toxoplasma gondii*, a sporozoan whose individual cells are 4 to 7 µm long. Diagnosis relies essentially on detection of specific antibodies in serum but the sites most commonly attacked are the lymph nodes, brain, eyes and lungs. Direct examination of sputum, vaginal exudates, spinal, pleural and peritoneal fluids are possible, but rarely practised. No diagnostic kits exist for direct examination of sputum and body fluids.

*Toxoplasma gondii* organisms were mixed with sputum, the sputum was liquefied and 1 ml passed on an 0.8 µm membrane fitted with a prefilter. The same procedure as in example 7 was followed. The results were excellent, with the detection of about 200 pathogenic entities in the sample.

EXAMPLE 10

Few diagnostic kits for the detection of *Neisseria gonorrhoeae* are available. The laboratory diagnosis of gonococcal infection is based primarily on the identification of the etiologic agent by microscopic examination and by culture. Cultures derived from sterile sites (cerebrospinal fluid, blood, synovial fluid) usually provide a definitive diagnostic but positive cultures from non-sterile sites are of uncertain value. No serologic test is commercially available yet.

Sputum was spiked with known concentrations of *Neisseria gonorrhoeae* antigen, as in example 5.The pore-size of the retaining membrane was 0.45 µm, compatible with the size of the organisms (0.6 to 1.0 µin diameter). The solubilisation of the sputum was done with 0.2% Sodium dodecyl sulphate at pH 9.5, treatment that was found not to alter the immunoreactivity of the pathogen. The presence of *N. gonorrhoeae*-specific rabbit IgG on the surface of the membrane, indicative of the presence of the pathogen, was further pursued as per example 7, with similar results.

EXAMPLE 11

The microscopic observation of the adult schizonts of *Plasmodium falciparum* in blood smears is the laboratory diagnostic of malaria.

Human fresh whole blood was spiked with formalin-inactivated schizonts. After the spiking, the blood was hemolysed with 1% Nonidet P 40 (final concentration) and 500 µl of the fluid was passed on a glass prefilter and collected on a retaining membrane with pore size 0.8 µm. Guanidine at a 4 molar concentration at pH 8.0 was found satisfactory in this analysis. A high concentration of 8 molar urea was also found adequate but this remarkable resistance of the schizonts may have been obtained by their fixation with formalin. The mouse antibodies used to label the antigen were revealed with Gold-labelled Protein G. Distinct red spots on the membrane signalled the presence of individual organisms.

A great number of possibilities were investigated, using either antibodies labelled with peroxidase or with gold, using protein A and protein G labelled with gold or with peroxidase, and the usefulness of secondary amplification steps was also investigated. The most reliable and easy method was found to be the one described in example 7: 500 µl to 1.5 ml (depending on the proteinic load of the processed sample) of sample is passed through a retaining membrane. The organisms presumably concentrated on the surface of the membrane are then treated with a solution 6 molar in guanidine hydrochloride at pH 8.After a wash, the membrane is treated with rabbit antibodies against the analyte and the presence of the antibodies potentially attached to the antigenic determinants of the analyte are put in evidence with gold-labelled protein A.

EXAMPLE 12

A treatment of the analysed sample directly with high concentrations of a chaotropic agent, before the concentration of the analyte on the retaining surface of a filtering membrane, possibly followed by a washing with the chaotropic agent, yields the best results.

100 µl of sputum found positive for TB by a microscopic examination were solubilised with 100 µl of solubilising solution consisting of 5% N-acetylcysteine and 0.5% mercaptoethanol in 1% NaOH brought at pH 12. This solubilising solution is standard procedure but other solubilising methods (e.g. sodium hyposulphite) known by the person skilled in the art are equally applicable.

After the sputum has been digested (5 minutes at room temperature), the sample is mixed with 1.3 ml of a solution 7 molar in guanidine at pH 8.5 containing 0.01% Tween 20, and processed as per example 7.

A red central spot is observed after completion of the test, not observable when negative samples are processed in an identical manner.

EXAMPLE 13

100 µl of sputum found positive for TB by a microscopic analysis was mixed with 100 µl of a solution that was 7 molar in guanidine at pH 12.00. After solubilisation of the sputum, 100 µl of NaClO at 12° was added to the mixture and digestion of the sputum was pursued during 15 minutes at Room Temperature. The sample was thereafter mixed with 1.3 ml of a solution that was 7 molar in guanidine at pH 8.5 and processed as per example 12.

A red central spot is observed after completion of the test, not observable when negative samples are processed in an identical manner.

What is claimed is:

1. A method for the detection of one of several types of microorganisms in a liquid sample suspected of containing microorganisms, comprising the steps of:
   (a) adding to said liquid sample a reagent solution comprising a chaotropic substance having a concentration between about 4 and about 8 M to produce a mixture;
   (b) filtering said mixture through a filter having a pore size which is small enough to prevent passage of microorganisms through the filter but large enough to permit passage of soluble material present in said mixture, whereby any microorganisms are retained on the filter, and
   (c) passing one or more labelled reagents through the filter to produce labeled microorganisms, wherein at least one of said reagents is specific for the microorganisms to be detected, and
   (d) detecting said labeled microorganisms.

2. The method according to claim 1, wherein the pH of the reagent solution comprising the chaotropic agent is at a pH of between about 6.0 and about 12.

3. The method according to claim 2, wherein the pH of the reagent solution comprising the chaotropic agent is about pH 9.0.

4. The method according to claim 1, wherein said liquid sample is obtained from an animal or human patient and is selected from the group consisting of sputum, blood, serum, plasma, cephalo-rachidian fluid, pericardial fluid, cerebrospinal fluid, vaginal exudates, spinal fluid, pleural fluid, peritoneal fluid, synovial fluid and urine.

5. The method according to claim 1, wherein said microorganisms are pathogenic bacteria or pathogenic eukaryotic parasites.

6. The method according to claim 1, wherein said microorganisms are detected simultaneously or successively.

7. The method according to claim 1, wherein said filter is a membrane made of nitrocellulose or nylon.

8. The method according to claim 1, wherein said chaotropic substance is selected from the group consisting of urea, guanidine, thiourea, isothiocyanate and a mixture thereof.

9. The method according to claim 1, wherein the labelled reagents specific for the microorganisms to be detected are antibodies.

10. A kit for the detection of one or more microorganisms in a sample suspected of containing microorganisms, comprising a filter having a pore size which is small enough to prevent passage of microorganisms through the filter but large enough to permit passage of any soluble material in the sample, one or several chaotropic substances in solution wherein the one or several chaotropic substances have a concentration between about 4 and about 8 M, and one or several labeling reagents, wherein said one or several labeling reagents are antibodies specific for the microorganisms to be detected.

11. The kit according to claim 10, wherein said one or several chaotropic substances are selected from the group consisting of urea, guanidine, thiourea, isothiocyanate and a mixture thereof.

12. The method according to claim 9, wherein said antibodies are coupled directly or indirectly to a marker.

13. The method according to claim 12, wherein said marker is selected from the group consisting of gold, micellae, enzymes, chromophores, stained latex beads, fluorophores, and a mixture thereof.

14. A method for the detection of one or several types of microorganisms in a liquid sample suspected of containing microorganisms, comprising the steps of:
   (a) filtering the liquid sample through a filter having a pore size which is small enough to prevent passage of microorganisms through the filter but large enough to permit passage of any soluble material present in the sample, whereby the microorganisms are retained on the filter;
   (b) passing a reagent solution comprising a chaotropic substance through the filter having any microorganisms retained thereon, said chaotropic reagent solution having a concentration between about 4 and about 8 M; and
   (c) passing one or more labelled reagents through the filter having the chaotropic-contacted microorganisms retained thereon, to produce labelled chaotropic-contacted microorganisms, wherein at least one of said reagents is specific for the microorganisms to be detected, and
   (d) detecting said labeled microorganisms.

15. The method according to claim 14, wherein the pH of the reagent solution comprising the chaotropic reagent is at a pH of between about 6.0 and about 12.

16. The method according to claim 15, wherein the pH of the reagent solution comprising the chaotropic reagent is about pH 9.0.

17. The method according to claim 16, wherein said liquid sample is obtained from an animal or human patient and is selected from the group consisting of sputum, blood, serum, plasma, cephalo-rachidian fluid, pericardial fluid, cerebrospinal fluid, vaginal exudates, spinal fluid, pleural fluid, peritoneal fluid, synovial fluid and urine.

18. The method according to claim 16, wherein said microorganisms are pathogenic bacteria or pathogenic eukaryotic parasites.

19. The method according to claim 16, wherein said microorganisms are detected simultaneously or successively.

20. The method according to claim 16, wherein said filter is a membrane made of nitrocellulose or nylon.

21. The method according to claim 16, wherein said chaotropic substance is selected from the group consisting of urea, guanidine, thiourea, isothiocyanate and a mixture thereof.

22. The method according to claim 16, wherein the labelled reagents specific for the microorganisms to be detected are antibodies.

23. The method according to claim 22, wherein said antibodies are coupled directly or indirectly to a marker.

24. The method according to claim 23, wherein said marker is selected from the group consisting of gold, micellae, enzymes, chromophores, stained latex beads, fluorophores, and a mixture thereof.

* * * * *

UNITED STATES PATENT AND TRADEMARK OFFICE
CERTIFICATE OF CORRECTION

PATENT NO. : 6,846,648 B2
DATED : January 25, 2005
INVENTOR(S) : Roland Maes

It is certified that error appears in the above-identified patent and that said Letters Patent is hereby corrected as shown below:

Column 11,
Lines 16 and 19, delete "labeled" insert -- labelled --.
Line 54, after "several" delete "labeling" and insert -- labelling --.
Lines 54-55, after "or several" delete "label-ing" and insert -- labelling --.

Column 12,
Line 26, delete "labeled" insert -- labelled --.

Signed and Sealed this

Thirteenth Day of June, 2006

JON W. DUDAS
*Director of the United States Patent and Trademark Office*